(12) United States Patent
Hayakawa et al.

(10) Patent No.: US 11,090,015 B2
(45) Date of Patent: Aug. 17, 2021

(54) DIAGNOSTIC X-RAY APPARATUS

(71) Applicant: Shimadzu Corporation, Kyoto (JP)

(72) Inventors: Toru Hayakawa, Kyoto (JP); Hajime Takemoto, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 26 days.

(21) Appl. No.: 16/649,103

(22) PCT Filed: Jul. 10, 2018

(86) PCT No.: PCT/JP2018/026015
§ 371 (c)(1),
(2) Date: Mar. 19, 2020

(87) PCT Pub. No.: WO2019/069521
PCT Pub. Date: Apr. 11, 2019

(65) Prior Publication Data
US 2020/0222015 A1   Jul. 16, 2020

(30) Foreign Application Priority Data
Oct. 3, 2017   (JP) .............................. JP2017-193312

(51) Int. Cl.
*A61B 6/00*   (2006.01)
(52) U.S. Cl.
CPC ............ *A61B 6/447* (2013.01); *A61B 6/4405* (2013.01); *A61B 6/4464* (2013.01)

(58) Field of Classification Search
CPC ....... A61B 6/40; A61B 6/4405; A61B 6/4464; A61B 6/447
See application file for complete search history.

(56) References Cited

U.S. PATENT DOCUMENTS

| | | | | |
|---|---|---|---|---|
| 3,575,368 A | * | 4/1971 | Thomas | ............... F16M 11/046 248/572 |
| 2019/0069860 A1 | * | 3/2019 | Takemoto | ............ A61B 6/4405 |

FOREIGN PATENT DOCUMENTS

| | | |
|---|---|---|
| JP | 2009-005909 A | 1/2009 |
| WO | 2017/149672 A1 | 12/2018 |

OTHER PUBLICATIONS

Written Opinion for PCT application PCT/JP2018/026015 dated Oct. 9, 2018, submitted with a machine translation.
"Medical Imaging and Radiological Equipment Handbook Revision 7", Japan Medical Imaging System Engineering Association, Mar. 31, 2007, p. 26, 1.3.5.2, submitted with table of contents (pp. (1) to (12), publication data (last page) and a machine translation of section 1.3.5.2.

* cited by examiner

*Primary Examiner* — Dani Fox
(74) *Attorney, Agent, or Firm* — Muir Patent Law, PLLC

(57) ABSTRACT

In this diagnostic X-ray apparatus (1), a radius of a spiral pulley (63) is set to a radius that differs from a radius of an Archimedes' spiral so that a tensile force of the spring member (61) applied to a second wire rope (67b) and a weight on an X-ray generation unit (50) side applied to a first wire rope (67a) are balanced.

7 Claims, 11 Drawing Sheets

DIAGNOSTIC X-RAY APPARATUS

TECHNICAL FIELD

The present invention relates to a diagnostic X-ray apparatus, and more specifically to a diagnostic X-ray apparatus equipped with a vertically movable X-ray generation unit.

BACKGROUND OF THE INVENTION

Conventionally, a diagnostic X-ray apparatus equipped with a vertically movable X-ray generation unit is known. Such a diagnostic X-ray apparatus is disclosed, for example, in the "Medical Imaging and Radiation Equipment Handbook", Revised Seventh Edition, 2007, P. 26, supervised by Japan Medical Imaging and Radiological Systems Industries Association.

The above-mentioned "Medical Imaging and Radiation Equipment Handbook" discloses an X-ray tube device equipped with an X-ray generation unit movable in the vertical direction. The X-ray tube device is provided with a spring member suspended from a ceiling, a circular pulley and a spiral pulley arranged on a floor surface, and an X-ray generation unit suspended from the ceiling. The tensile force of the spring member is applied to the wire rope wound around the circular pulley. The weight of the X-ray generation unit is applied to the wire rope wound around the spiral pulley. In accordance with the upward and downward movement of the X-ray generation unit, the wire rope is wound around the spiral pulley (or the wire rope is unwound from the spiral pulley).

In cases where the spiral of the spiral pulley is an Archimedes' spiral (a spiral in which the radius increases in proportion to the rotation), at any height of the X-ray generation unit, the tensile force of the spring member applied to the wire rope wound around the circular pulley and the weight of the X-ray generation unit applied to the wire rope wound around the spiral pulley are constantly balanced. As a result, the X-ray generation unit can be immobilized at any height position.

However, in the X-ray tube device described in the above-mentioned "Medical Imaging and Radiographic Equipment Handbook", since the X-ray generation unit is connected to the wire rope wound around the spiral pulley, the wire rope wound around the spiral pulley moves in the rotation axis direction of the spiral pulley and also moves in a direction crossing the rotation axis direction of the spiral pulley as the X-ray generation unit moves upward and downward. For this reason, in cases where the spiral pulley is placed in a supporting unit supporting the X-ray tube device, the portion of the spiral pulley on which the wire rope is wound (or the portion of the spiral pulley from which the wire rope is unwound) needs to be exposed from the supporting unit. As a result, there is a disadvantage that the X-ray tube device becomes relatively large.

To solve this inconvenience, conventionally, an X-ray tube device is known in which the tensile force of the spring member is applied to the wire rope wound around the spiral pulley and the weight of the X-ray generation unit is applied to the wire rope connected to the circular pulley (i.e., in the X-ray tube device described in "Medical Imaging and Radiology Equipment Handbook", it is configured such that the arrangement of the spiral pulley and that of the circular pulley is changed). In this conventional X-ray tube device, as the X-ray generation unit moves upward and downward, the wire rope moves in the rotation axis direction of the circular pulley but does not move in a direction crossing the rotation axis direction of the circular pulley. This eliminates the need to increase the portion of the circular pulley exposed from the supporting unit that supports the X-ray generation unit. As a result, an increase in the size of the X-ray tube device can be suppressed.

PRIOR ART DOCUMENT

Patent Document

Non-Patent Document 1: "Medical Imaging and Radiation Equipment Handbook", supervised by Japan Medical Imaging and Radiological Systems Industries Association, Revised Seventh Edition, 2007, p. 26

SUMMARY OF THE INVENTION

Problems to be Solved by the Invention

However, in a conventional X-ray tube device in which the tensile force of the spring member is applied to the wire rope wound around the spiral pulley, in cases where the spiral of the spiral pulley is an Archimedes' spiral (a spiral in which the radius increases in proportion to the rotation of the spiral pulley), there is a case in which the tensile force of the spring member applied to the spiral pulley and the weight of the X-ray generation unit applied to the circular pulley is not balanced. In this case, there is a disadvantage that a relatively large force is required when the user moves the X-ray generation unit upward and downward in the vertical direction. As a result, the burden on the user to move the X-ray generation unit upward and downward in the vertical direction increases.

The present invention has been made to solve the above-mentioned problems, and an object of the present invention is to provide a diagnostic X-ray apparatus capable of reducing a burden when a user moves an X-ray generation unit upward and downward in a vertical direction while suppressing an increase in the size of a diagnostic X-ray apparatus.

Means for Solving the Problem

In order to achieve the aforementioned object, the diagnostic X-ray apparatus according to one aspect of the present invention, includes:

an X-ray generation unit including an X-ray source for irradiating a subject with X-rays, the X-ray generation unit being movable upward and downward in a vertical direction;

a spring member that expands and contracts as the X-ray generation unit is moved upward and downward;

a circular pulley in which a weight on the X-ray generation unit side is applied to a first wire rope wound around the circular pulley, a radius of the circular pulley being constant; and a spiral pulley coaxially connected to the circular pulley in a manner as to be rotatable integrally with the circular pulley, a tensile force of the spring member being applied to a second wire rope wound around the spiral pulley, and a radius of the spiral pulley changing in a spiral manner, wherein the radius of the spiral pulley is set to a radius that differs from a radius of an Archimedes' spiral so that the tensile force of the spring member applied to the second wire rope and the weight on the X-ray generation unit side applied to the first wire rope are balanced. Note that the "spiral" means swirling like a line of a snail shell.

In the diagnostic X-ray apparatus according to one aspect of the present invention, as described above, since the weight on the X-ray generation unit side is applied to the first wire rope wound around the circular pulley having a constant radius, as the X-ray generation unit is moved upward and downward, the first wire rope moves in the rotation axis direction of the circular pulley while not moving in a direction crossing the rotation axis direction of the circular pulley. With this, there is no need to increase the size of the portion of the circular pulley to be exposed, so that it is possible to suppress an increase in the size of the diagnostic X-ray apparatus. In addition, by setting the radius of the spiral pulley to a radius (a radius that changes in a spiral manner) that differs from the radius of the Archimedes' spiral so that the tensile force of the spring member applied to the second wire rope and the weight on the X-ray generation unit side applied to the first wire rope are balanced (or a state closed to the balanced state), the tensile force of the spring member applied to the second wire rope and the weight on the X-ray generation unit side applied to the first wire rope become balanced (or close to the balanced state), the user can move the X-ray generation unit upward and downward in the vertical direction with a relatively small force. As a result, it is possible to reduce the burden when the user moves the X-ray generation unit upward and downward in the vertical direction. This makes it possible to reduce the burden when the user moves the X-ray generation unit upward and downward in the vertical direction while suppressing the increase in the size of the diagnostic X-ray apparatus.

In the diagnostic X-ray apparatus according to the aforementioned one aspect of the present invention, preferably, when the radius of the spiral pulley is R, the radius of the circular pulley is r, the weight on the X-ray generation unit side is W, a spring constant of the spring member is k, an amount of change in a length of the spring member is x, an initial amount of change in the length of the spring member is $x_0$, and a rotation angle of the spiral pulley is θ, the radius of the spiral pulley is set to a radius that differs from the radius of the Archimedes' spiral based on the Expression (1) described below.

$$Wr = kR\left(\int_0^\theta \sqrt{R^2 + \left(\frac{dR}{d\theta}\right)^2}\, d\theta + x_0\right) \quad (1)$$

With this configuration, by setting the radius R (spirally changing radius) of the spiral pulley (set to a radius that differs from the radius of the Archimedes' spiral) so as to satisfy the Expression (1), the tensile force of the spring member applied to the second wire rope and the weight on the X-ray generation unit side applied to the first wire rope can be easily balanced.

In this case, preferably, when the radius R of the spiral pulley is approximated by any one of approximate expressions of a polynomial function, a logarithmic function, and an exponential function of a second-degree or more, a force of deviation from a state in which the tensile force of the spring member applied to the second wire rope and the weight on the X-ray generation unit side applied to the first wire rope are balanced is defined as F, a coefficient included in the approximate expression is defined so that the force F of deviation is substantially zero in the Expression (2) described below.

$$(W+F)r = kR\left(\int_0^\theta \sqrt{R^2 + \left(\frac{dR}{d\theta}\right)^2}\, d\theta + x_0\right) \quad (2)$$

With this configuration, even if the radius R of the spiral pulley cannot be strictly set based on the Expression (1), the radius R (spirally changing radius) of the spiral pulley in which the tensile force of the spring member applied to the second wire rope and the weight on the X-ray generation unit side applied to the first wire rope are substantially balanced can be set by using an approximate expression.

In the diagnostic X-ray apparatus in which the radius R of the aforementioned spiral pulley is approximated by an approximate expression, when the radius R of the spiral pulley is approximated by a polynomial function of a third-degree shown in the Expression (3) described below and a number of unknown coefficients a, b, c, and d included in the Expression (3) described below is reduced based on a boundary condition of a rotation angle of the spiral pulley, the coefficient included in an approximate expression is determined so that the force F of deviation becomes substantially zero in the Expression (2) described above.

$$R = f(\theta) = a\theta^3 + b\theta^{12} + c\theta^1 + d \quad (3)$$

With this configuration, as compared with the case in which the radius R of the spiral pulley is approximated by a polynomial function of a second-order, the radius R of the spiral pulley in which the tensile force of the spring member applied to the second wire rope and the weight on the X-ray generation unit side applied to the first wire rope are balanced can be set more accurately. Further, since the number of unknown coefficients a, b, c, and d is reduced based on the border condition of the rotation angle of the spiral pulley, the unknown coefficients can be easily calculated.

In the diagnostic X-ray apparatus according to the aforementioned one aspect of the present invention, preferably, the diagnostic X-ray apparatus further includes a booster mechanism arranged between the spring member and the spiral pulley, the booster mechanism including a booster pulley, wherein when the radius of the spiral pulley is R, the radius of the circular pulley is r, the weight on the X-ray generation unit side is W, a spring constant of the spring member is k, an amount of change in a length of the spring member is x, an initial amount of change in the length of the spring member is $x_0$, a rotation angle of the spiral pulley is θ, and a constant number by a booster is C, the radius of the spiral pulley is set to a radius that differs from the radius of the Archimedes' spiral based on the Expression (4) described below.

$$Wr = CkR\left(\int_0^\theta \sqrt{R^2 + \left(\frac{dR}{d\theta}\right)^2}\, d\theta + x_0\right) \quad (4)$$

With this configuration, in the diagnostic X-ray apparatus equipped with a booster mechanism, it is also possible to set the radius R (spirally changing radius) in which the tensile force of the spring member applied to the second wire rope and the weight on the X-ray generation unit side applied to the first wire rope are balanced by using Equation (4), in the same manner as in the diagnostic X-ray apparatus not equipped with a booster mechanism.

In the diagnostic X-ray apparatus according to the aforementioned one aspect of the present invention, preferably, the diagnostic X-ray apparatus further includes a supporting unit in which the spring member, the circular pulley, and the spiral pulley is accommodated, a diagnostic X-ray apparatus main body to which the supporting unit is attached, and a wheel capable of making the diagnostic X-ray apparatus main body movable. With this configuration, it is possible to reduce a burden when the user moves the X-ray generation unit upward and downward in the vertical direction in the movable diagnostic X-ray apparatus.

In the diagnostic X-ray apparatus according to the aforementioned one aspect of the present invention, preferably, the diagnostic X-ray apparatus further includes a supporting unit in which the spring member, the circular pulley, and the spiral pulley are accommodated, wherein the supporting unit is arranged in a state of being suspended from a ceiling. With this configuration, in the diagnostic X-ray apparatus equipped with the supporting unit suspended from a ceiling, it is possible to reduce a burden when the user moves the X-ray generation unit upward and downward in the vertical direction. Further in the diagnostic X-ray apparatus suspended from a ceiling, in general, the wire rope is passed through the inside of the supporting unit suspended from the ceiling and is connected to the X-ray generation unit. Thus, by configuring such that the weight on the X-ray generation unit side is applied to the wire rope wound around the circular pulley having a constant radius as in the present invention, it is possible to suppress the contact with the inner surface of the supporting unit because the wire rope does not move in a direction crossing the rotational axis direction of the wire rope wound around (unwound from) the circular pulley.

Effects of the Invention

According to the present invention, as described above, it is possible to reduce the burden when the user moves the X-ray generation unit upward and downward in the vertical direction while suppressing the increase in the size of the diagnostic X-ray apparatus.

EMBODIMENTS FOR CARRYING OUT THE INVENTION

Hereinafter, embodiments in which the present invention is embodied will be described with reference to the attached drawings.

First Embodiment

With reference to FIG. 1 to FIG. 10, a configuration of a diagnostic X-ray apparatus 1 according to a first embodiment will be described.

(Entire Configuration of Diagnostic X-Ray Apparatus)

Figure 1:
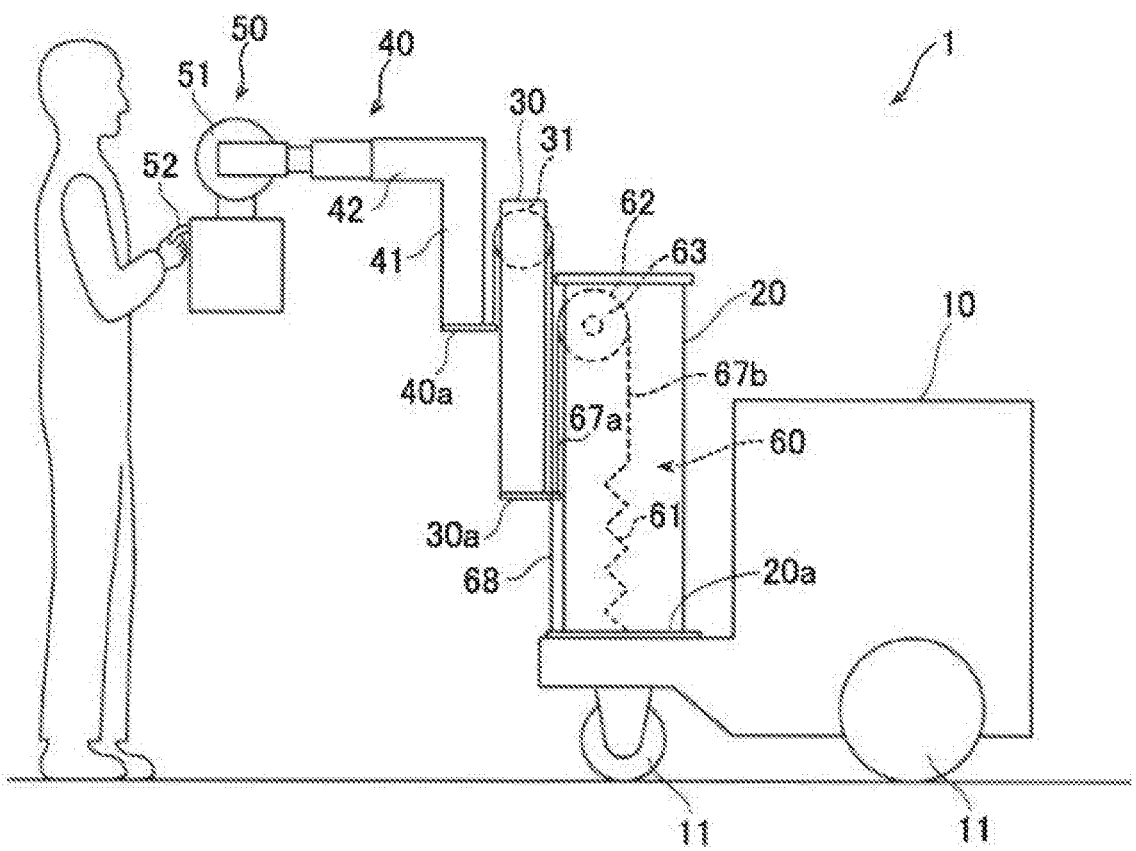
FIG. 1 is a diagram showing a configuration of a diagnostic X-ray apparatus according to a first embodiment.

As shown in FIG. 1, a diagnostic X-ray apparatus 1 is configured so that the entire device is movable and X-ray imaging can be performed by moving the device to a patient (subject) in each hospital room at the time of rounds. The diagnostic X-ray apparatus 1 is provided with a main body 10, a supporting unit 20, an intermediate supporting unit 30, an X-ray tube holding unit 40, and an X-ray generation unit 50. Note that the main body 10 is an example of the "diagnostic X-ray apparatus main body" recited in claims.

The main body 10 is provided with a power supply device, a battery, an operating panel, and the like. A plurality of wheels 11 for allowing the diagnostic X-ray apparatus 1 to move is provided at the lower portion of the main body 10.

The supporting unit 20 is attached to the front portion of the main body 10 so as to extend in the vertical direction. The supporting unit 20 has a hollow interior, and is configured to accommodate a balance mechanism 60 (a spring member 61, a wire rope 67a, a wire rope 67b, a circular pulley 62, and a spiral pulley 63, which will be described later) that enables the intermediate supporting unit 30 to be moved upward and downward in a state in which the intermediate supporting unit 30 is kept balanced. The wire rope 67a and the wire rope 67b are an example of the "first wire rope" and that of the "second wire rope" recited in claims, respectively.

The intermediate supporting unit 30 is mounted in a vertically movable manner on the front side of the supporting unit 20. A circular (constant in radius) pulley 31 is provided inside the intermediate supporting unit 30.

The X-ray tube holding unit 40 is mounted in a vertically movable manner on the front side of the intermediate supporting unit 30. The X-ray tube holding unit 40 is formed in a generally L-shape (having a vertically extending portion 41 and a horizontally extending portion 42).

The X-ray generation unit 50 is attached to the tip end of the portion 42 of the X-ray tube holding unit 40. The X-ray generation unit 50 is provided with an X-ray tube 51. The X-ray tube 51 can change the height position in accordance with the upward and downward movement of the X-ray tube holding unit 40. The X-ray generation unit 50 is provided with a handle portion 52 for a user to grip to move the X-ray generation unit 50 upward and downward. Note that the X-ray tube 51 is an example of the "X-ray source" recited in claims.

(Configuring Balance Mechanism)

Figure 2:
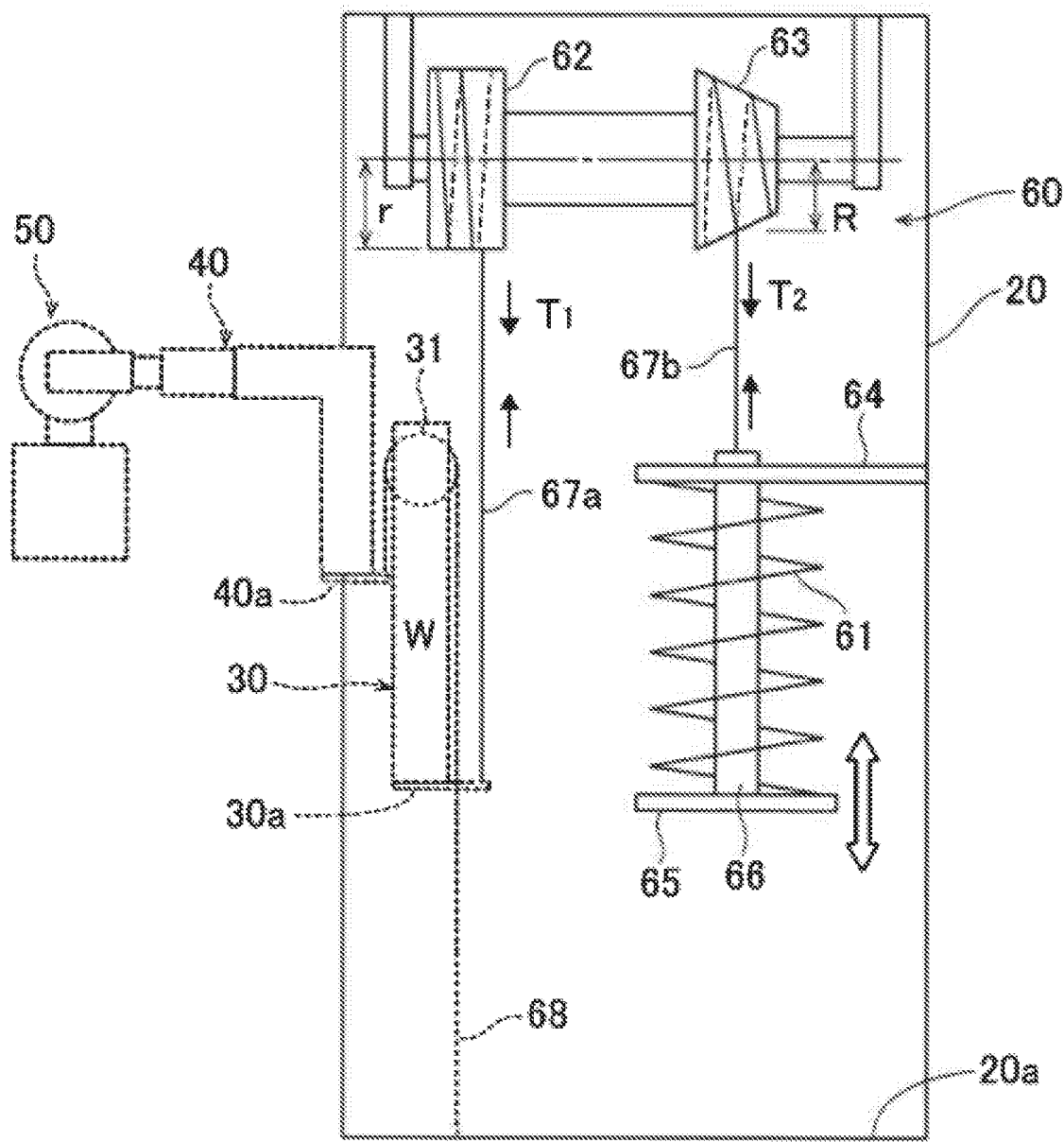
FIG. 2 is a diagram showing a configuration of a balance mechanism of the diagnostic X-ray apparatus according to the first embodiment.

Next, with reference to FIG. 2, the configuration of the balance mechanism 60 will be described. FIG. 2 is a schematic diagram of the balance mechanism 60. Note that in FIG. 2, for the sake of clarifying the description, the circular pulley 62 and the spiral pulley 63 are connected to a rotating shaft in a separated state, however, in reality, the circular pulley 62 and the spiral pulley 63 are integrally formed so that the circular pulley 62 and the spiral pulley 63 adjoin each other (see FIG. 6).

As shown in FIG. 2, the balance mechanism 60 includes the spring member 61, the circular pulley 62, and the spiral pulley 63.

The spring member 61 is composed of a compressive spring. The upper end of the spring member 61 is fixed to an upper spring seat 64. The upper spring seat 64 is fixed to the inside of the supporting unit 20. The lower end of the spring member 61 is fixed to a lower spring seat 65. The lower spring seat 65 is movably arranged within the supporting unit 20. A shaft 66 is attached to the center of the lower spring seat 65. The shaft 66 extends through a hole (not shown) in the upper spring seat 64 and projects from the top surface of the upper spring seat 64. The shaft 66 is configured to be vertically movable through the hole of the upper spring seat 64. The spring member 61 is arranged between the upper spring seat 64 and the lower spring seat 65 with the shaft 66 penetrating the inside of the spring member 61. The spring member 61 is configured to extend and retract in accordance with the upward and downward movement of the X-ray generation unit 50.

The circular pulley 62 is configured so that the radius r is constant. The wire rope 67a is wound around the circular pulley 62. The wire rope 67a is connected (fixed) to the bottom portion 30a of the intermediate supporting unit 30. The weight of the X-ray generation unit 50 is applied to the wire rope 68 wound around a circular pulley 31 provided to the intermediate supporting unit 30. Specifically, one end of the wire rope 68 is connected (fixed) to the bottom portion 20a of the supporting unit 20, and the other end thereof is connected (fixed) to the bottom portion 40a of the X-ray tube holding unit 40. As a result, the weight W on the X-ray generation unit 50 (intermediate supporting unit 30) side is applied to the wire rope 67a wound around the circular pulley 62.

The spiral pulley 63 is configured so that the radius R changes spirally. The spiral pulley 63 is rotatably and coaxially connected to the circular pulley 62. A wire rope 67b is wound around the spiral pulley 63. The wire rope 67b is connected to the shaft 66. As a result, the tensile force of the spring member 61 is applied to the wire rope 67b wound around the spiral pulley 63.

(Equilibration of Balance Mechanism)

The equilibration of the balance mechanism 60 of the first embodiment will now be described while comparing with the balance mechanism 160 of Comparative Example (a configuration in which the tensile force of the spring member 161 is applied to the circular pulley 162).

(Balance Mechanism By Comparative Example)

Figure 3:
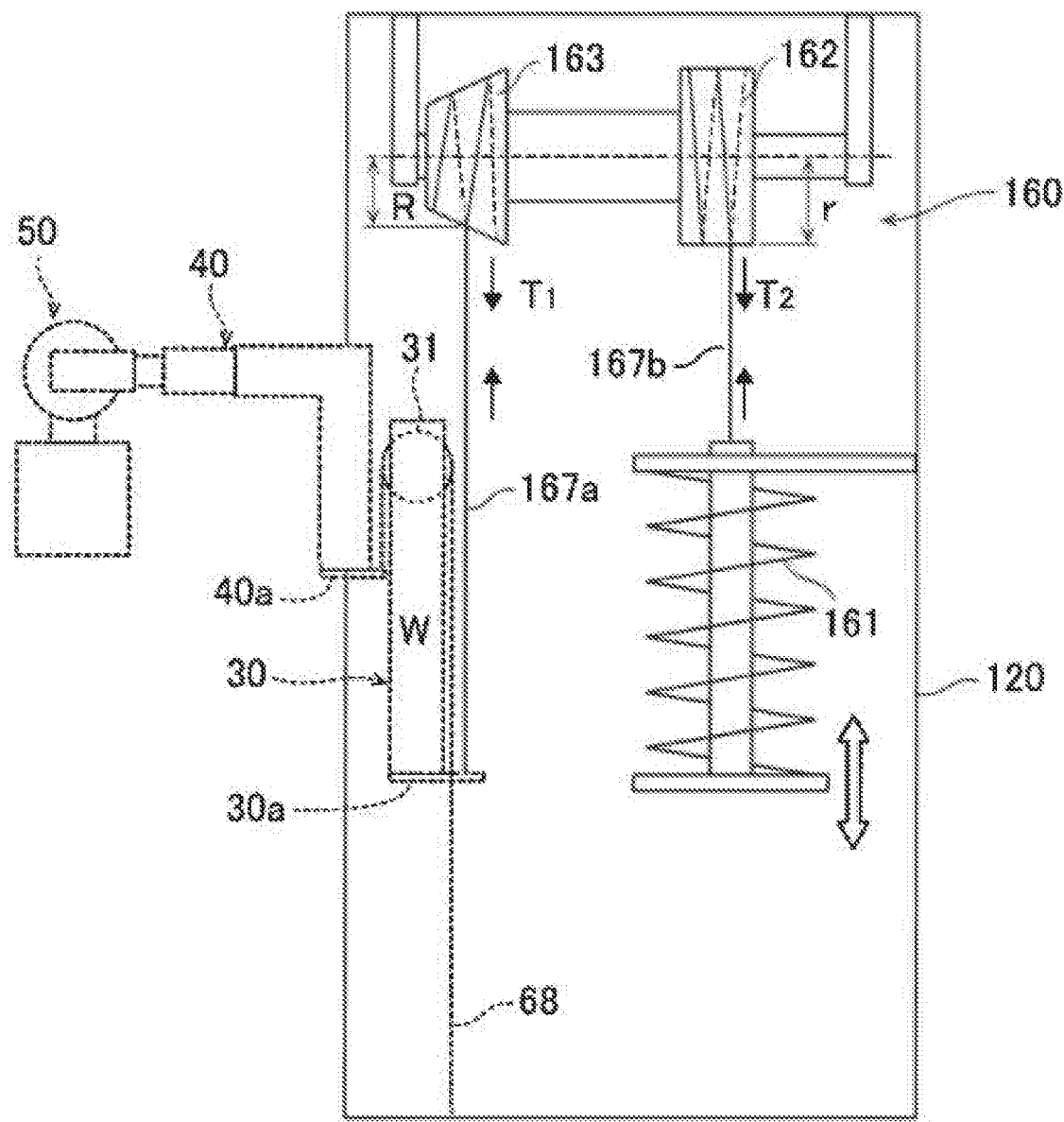
FIG. 3 is a diagram showing a configuration of a balance mechanism of a diagnostic X-ray apparatus according to Comparative Example.

As shown in FIG. 3, in the balance mechanism 160 according to Comparative Example, it is configured such that the tensile force of the spring member 161 is applied to the circular pulley 162 and the weight W on the X-ray generation unit 50 side is applied to the spiral pulley 163. Here, when the radius of the spiral pulley 163 is R [mm], the radius of the circular pulley 162 is r [mm], the tensile force of the wire rope 167a on the X-ray generation unit 50 side is $T_1$ [kgf], and the tensile force of the wire rope 167b on the spring member 161 side is $T_2$ [kgf], the Expression (5) described below is established due to the balance of the torque about the rotating shaft.

$$T_1 R = T_2 r \tag{5}$$

With respect to the tensile force $T_1$ [kgf] of the wire rope 167a on the X-ray generation unit 50 side, the Expression (6) described below is established by using the weight W [kgf] on the X-ray generation unit 50 side.

$$T_1 = W \tag{6}$$

With respect to the tensile force $T_2$ [kgf] of the wire rope 167b on the spring member 161 side, the Expression (7) described below is established by using the spring constant k of the spring member 161 and the amount of compression x [mm] of the spring member 161.

$$T_2 = kx \tag{7}$$

Substituting the Expression (6) and the Expression (7) into the Expression (5) yields the Expression (8) described below.

$$WR = kxr \tag{8}$$

The amount of compression x [mm] of the spring member 161 is represented by the Expression (9) described below by using the radius r [mm] of the circular pulley 162, the rotation angle θ [rad] of the spiral pulley 163 and the circular pulley 162, and the initial amount of the compression $x_0$ [mm] of the spring member 161.

$$x = r\theta + x_0 \tag{9}$$

Substituting the Expression (9) into the Expression (8) and solving with the radius R of the spiral pulley 163 yields the Expression (10) and the Expression (11) described below.

$$WR = k(r\theta + x_0)r = kr^2\theta + kx_0 r \tag{10}$$

$$R = \frac{kr^2}{W}\theta + \frac{kx_0 r}{W} \tag{11}$$

In the Expression (11), since k, r, W, and $x_0$ are all constant, replacing these constants with coefficients a and b term by term yields the Expression (12) and the Expression (13) described below.

$$\frac{kr^2}{W} = a, \quad \frac{kx_0 r}{W} = b \tag{12}$$

$$R = a\theta + b \tag{13}$$

In the balance mechanism 160 according to Comparative Example, as will be apparent from the Expression (13), the radius R of the spiral pulley 163 increases in proportion to the rotation angle θ, so that the spiral of the spiral pulley 163 becomes the Archimedes' spiral. This ensures that the tensile force of the spring member 161 applied to the wire rope 167b and the weight W on the X-ray generation unit 50 side applied to the wire rope 167a are constantly balanced (equilibrated) because the tensile force by the spring member 161 increases in proportion to the rotation angle θ and the radius R of the spiral pulley 163 also increases in proportion to the rotation angle θ. This causes the X-ray generation unit 50 to stand still at the desired height position.

Figure 4:
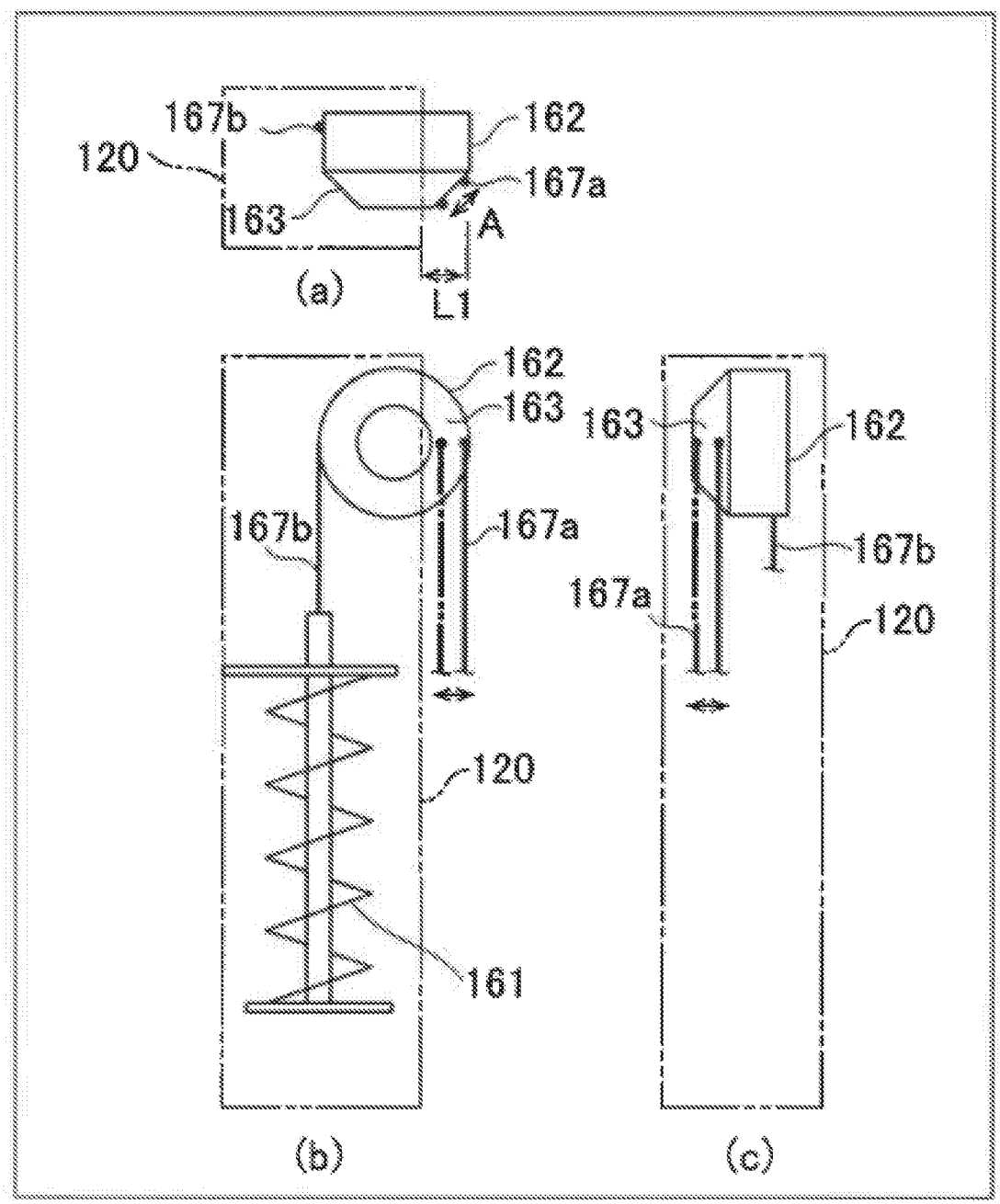
FIG. 4 is a diagram including a top view (a), a front view (b), and a side view (c) of the balance mechanism of the diagnostic X-ray apparatus according to Comparative Example.

As shown in FIG. 4, in the balance mechanism 160 according to Comparative Example, the X-ray generation unit 50 (see FIG. 3) is connected to the spiral pulley 163 via the wire rope 167a. Therefore, the winding position (unwinding position) of the wire rope 167a moves relatively largely along the direction A crossing the rotational axial direction of the spiral pulley 163 in accordance with the upward and downward movement of the X-ray generation unit 50. Therefore, in the balance mechanism 160, a portion of the spiral pulley 163 (a relatively large length L1, see (a) of FIG. 4) needs to be exposed from the supporting unit 120.

Figure 5:
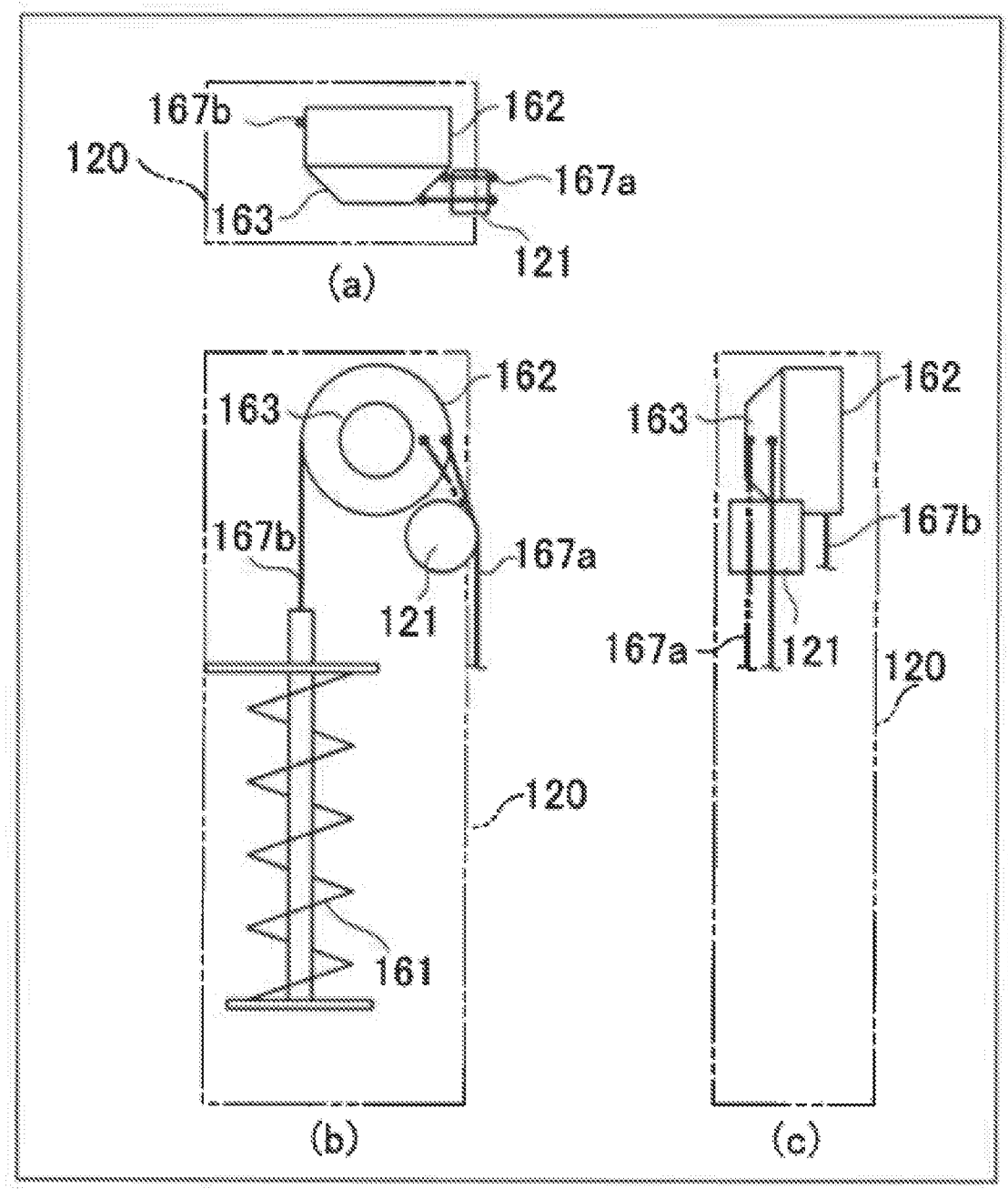
FIG. 5 is a diagram including a top view (a), a front view (b), and a side view (c) of a balance mechanism of a diagnostic X-ray apparatus according to Comparative Example equipped with an idler.

Further, as shown in FIG. 5, it is considered to use an idler 121 in order to reduce the exposed portion of the spiral pulley 163. However, when the idler 121 is used, the vertical size of the supporting unit 120 increases in order to maintain the amount of the upward and downward movement of the X-ray generation unit 50 (keep the same as when the idler 121 is not provided). Also, the wire rope 167a is damaged due to the friction between the wire rope 167a and the idler 121. Further, the number of components increases by the number of the idler 121.

Figure 6:
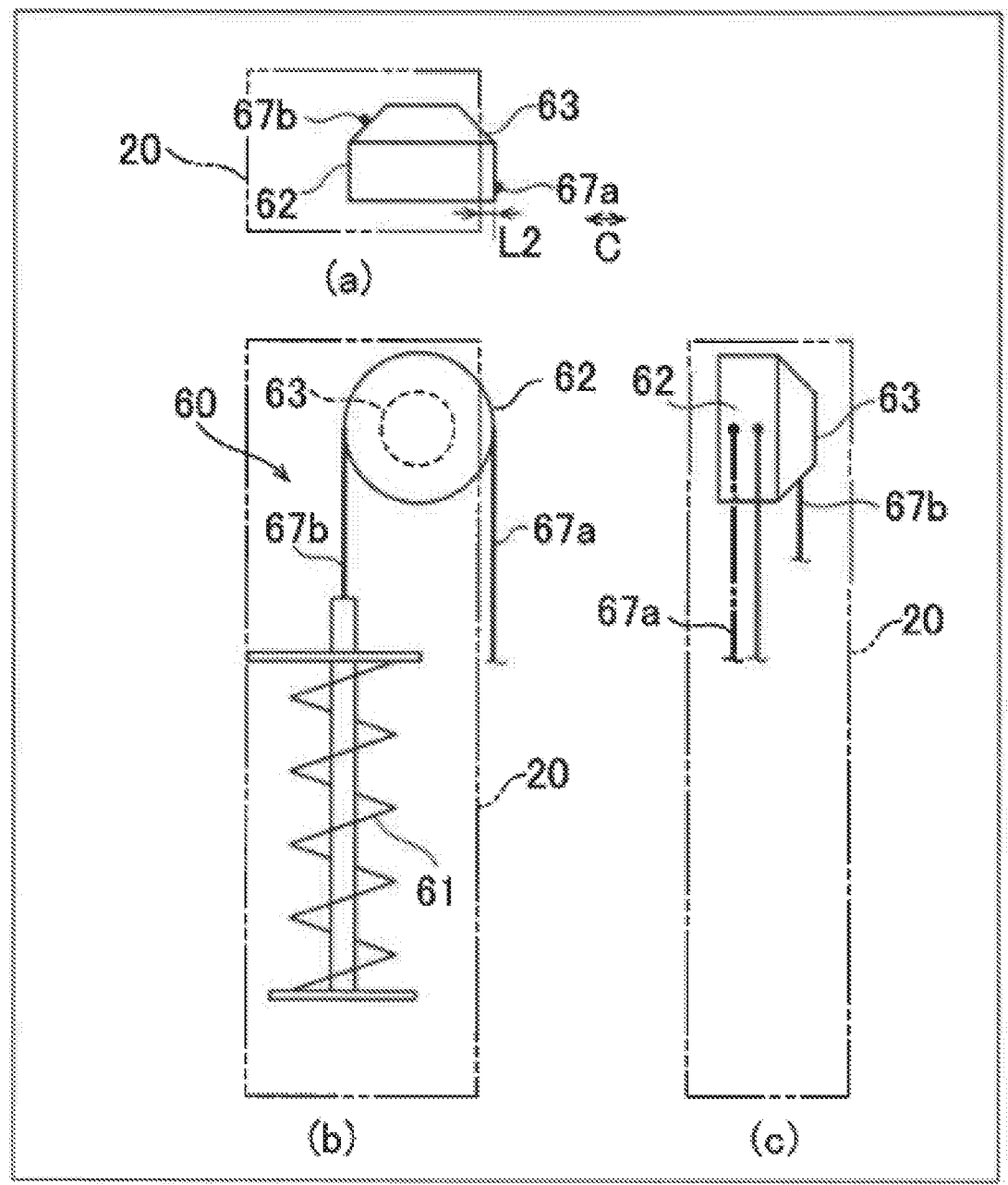
FIG. 6 is a diagram including a top view (a), a front view (b), and a side view (c) of the balance mechanism of the diagnostic X-ray apparatus according to the first embodiment.

On the other hand, as shown in FIG. 6, in the balance mechanism 60 according to the first embodiment, since the X-ray generation unit 50 (intermediate supporting unit 30) side is connected to the circular pulley 62 via the wire rope 67a, the winding position (unwinding position) of the wire rope 67a does not move in the C direction crossing (perpendicular to) the rotational axial direction of the spiral pulley 63 in accordance with the upward and downward movement of the X-ray generation unit 50. Therefore, in the balance mechanism 60, the exposed portion (length L2, see (a) of FIG. 6) of the circular pulley 62 from the supporting unit 20 is relatively small. Further, since no idler 121 need to be used, it is possible to suppress the enlargement of the diagnostic X-ray apparatus 1 and to suppress damages of the wire rope 67a caused by the friction with the idler 121. In addition, it is possible to suppress an increase in the number of parts.

(Balance Mechanism of First Embodiment)

Next, with reference to FIG. 2, the balance mechanism 60 according to the first embodiment will be described. In the balance mechanism 60 shown in FIG. 2, the tensile force of the wire rope 67a applied to the circular pulley 62 is a tensile force for lifting the intermediate supporting unit 30.

In the balance mechanism 60 according to the first embodiment, when the radius of the spiral pulley 63 is R [mm], the radius of the circular pulley 62 is r [mm], the tensile force of the wire rope 67a on the X-ray generation unit 50 side is $T_1$ [kgf], and the tensile force of the wire rope 67b on the spring member 61 side is $T_2$ [kgf], the Expression (14) described below is established due to the balance of the torque about the rotating shaft.

$$T_1 r = T_2 R \quad (14)$$

With respect to the tensile force $T_1$ [kgf] of the wire rope 67a on the X-ray generation unit 50 (intermediate supporting unit 30) side, the Expression (15) described below is established by using the weight W [kgf] on the X-ray generation unit 50 side.

$$T_1 = W \quad (15)$$

With respect to the tensile force $T_2$ [kgf] of the wire rope 67b on the spring member 61 side, the Expression (16) described below is established by using the spring constant k of the spring member 61 and the amount of compression x [mm] of the spring member 61.

$$T_2 = kx \quad (16)$$

Substituting the Expression (15) and the Expression (16) into the Expression (14) yields the Expression (17) described below.

$$Wr = kxR \quad (17)$$

The amount of compression x [mm] of the spring member 61 is equal to the initial amount of compression $x_0$ [mm] of the spring member 61 and the length of the wire rope 67b wound by the spiral pulley 63. The length of the wire rope 67b wound by the spiral pulley 63 is equal to the length of the spiral of the spiral pulley 63 (the length of the portion of the spiral on which the wound wire rope 67b is wound). So, the amount of compression x [mm] of the spring member 61 is expressed by the Expression (18) described below using the initial amount of compression $x_0$ [mm] of the spring member 61, the radius R [mm] of the spiral pulley 63, and the rotation angle θ [rad] of the spiral pulley 63.

$$x = \int_0^\theta \sqrt{R^2 + \left(\frac{dR}{d\theta}\right)^2}\, d\theta + x_0 \quad (18)$$

By substituting the Expression (18) into the Expression (17), the Expression (19) described below is obtained.

$$Wr = kR\left(\int_0^\theta \sqrt{R^2 + \left(\frac{dR}{d\theta}\right)^2}\, d\theta + x_0\right) \quad (19)$$

It is difficult to solve the Expression (19) with the radius R of the spiral pulley 63. Further, the radius R of the spiral pulley 63 does not become a polynomial of the first-order as in the Archimedes' spiral, in the same manner as in the balance mechanism 160 of Comparative Example. That is, in the balance mechanism 60 of the first embodiment, when the radius R of the spiral pulley 63 is formed to correspond to the Archimedes' spiral, the tensile force of the spring member 61 applied to the wire rope 67b and the weight W on the X-ray generation unit 50 side applied to the wire rope 67a are not balanced.

Therefore, in the first embodiment, the radius R of the spiral pulley 63 is set to a radius that differs from the radius of the Archimedes' spiral, so that the tensile force of the spring member 61 applied to the wire rope 67b and the weight W on the X-ray generation unit 50 side applied to the wire rope 67a are balanced. Specifically, the radius R of the spiral pulley 63 is set to a radius that differs from the radius of the Archimedes' spiral based on the Expression (19).

As described above, since it is difficult to solve the Expression (19) by the radius R of the spiral pulley 63, in the first embodiment, the radius R of the spiral pulley 63 is approximated by a polynomial function of a third-order as shown in the Expression (20) described below.

$$R = f(\theta) = a\theta^3 + b\theta^2 + c\theta + d \quad (20)$$

Since the Expression (20) is an approximate expression, the Expression (19) cannot be strictly satisfied. The right side of the Expression (19) increases or decreases with respect to the left side which is constant. Therefore, in the first embodiment, when the force of deviation from the condition in which the tensile force of the spring member 61 applied to the wire rope 67b and the weight W on the X-ray generation unit 50 side applied to the wire rope 67a are balanced is defined as F, the coefficients a, b, c, and d included in the approximate expression are defined so that the force F of deviation is substantially zero in the Expression (21) and the Expression (22) described below.

$$(W+F)r = kR\left(\int_0^\theta \sqrt{R^2 + \left(\frac{dR}{d\theta}\right)^2} \, d\theta + x_0\right) \quad (21)$$

$$F = \frac{kR}{r}\left(\int_0^\theta \sqrt{R^2 + \left(\frac{dR}{d\theta}\right)^2} \, d\theta + x_0\right) - W \quad (22)$$

By determining the plurality of coefficients a, b, c, and d such that the force F of deviation [kgf] approaches zero, the tensile force of the spring member 61 applied to the wire rope 67b and the weight W on the X-ray generation unit 50 side applied to the wire rope 67a become substantially balanced. This allows the user to move the X-ray generation unit 50 upward and downward without substantially recognizing the force F of deviation [kgf]. Note that the force F of deviation means an operating force by which the user grasps the handle portion 52 and moves the X-ray generation unit 50 in the vertical direction.

(How to Determine Coefficient)

Here, in the first embodiment, the coefficients included in the approximate expression are determined based on the boundary condition of the rotation angle θ of the spiral pulley 63 such that the force F of deviation becomes substantially zero in a state in which the number of unknown coefficients a, b, c, and d included in the Expression (20) is reduced. In particular, the number of unknown coefficients a, b, c, and d is reduced based on the boundary condition when the rotation angle θ [rad] becomes the minimum value 0 [rad] and the largest value θmax [rad].

Here, the maximum value $R_{max}$ [mm] of the radius R of the spiral pulley 63 is determined to be an arbitrary value based on the limit of the size of the supporting unit 20 in which the balance mechanism 60 is accommodated. Then, by substituting the rotation angle θ at the time of the maximum value $R_{Max}$ [mm] as the minimum value 0 [rad] into the Expression (20), the Expression (23) and the Expression (24) described below are obtained.

$$R_{max} = a \times \theta^3 + b \times \theta^2 + c \times 0 + d \quad (23)$$

$$d = R_{Max} \quad (24)$$

Further, the radius r of the circular pulley 62 is arbitrarily determined based on the size limitation of the supporting unit 20 in which the balance mechanism 60 is accommodated. The maximum value $\theta_{Max}$ [rad] of the rotation angle θ is expressed by the Expression (25) and the Expression (26) described below, using the radius r of the circular pulley 62 and the vertical stroke amount L [mm] of the X-ray generation unit 50 (intermediate supporting unit 30).

$$L = r\theta_{Max} \quad (25)$$

$$\theta_{Max} = \frac{L}{r} \quad (26)$$

Here, for the wire rope 67a (wire rope 67b) used in the diagnostic X-ray apparatus 1, the diameter of the wire rope 67a (wire rope 67b), the diameter of the element wire thereof, and the smallest radius of the pulley that can be combined are defined by a standard or the like. Therefore, the minimum radius $R_{min}$ [mm] of the spiral pulley 63 is determined to any value within the range of the minimum radius determined by the standard or the like. The Expression (27) described below is obtained by substituting the Expression (24) and the Expression (26) into the Expression (20) when the rotation angle θ when the radius R of the spiral pulley 63 is the minimum radius $R_{min}$ [mm] is defined as the maximum value $\theta_{Max}$.

$$R_{min} = a\left(\frac{L}{r}\right)^3 + b\left(\frac{L}{r}\right)^2 + c\left(\frac{L}{r}\right) + R_{Max} \quad (27)$$

When the Expression (27) is solved with the coefficient a, the Expression (28) described below is obtained.

$$a = -\left(\frac{r}{L}b + \left(\frac{r}{L}\right)^2 c + \left(\frac{r}{L}\right)^3 (R_{Max} - R_{min})\right) \quad (28)$$

Substituting the Expression (24) and the Expression (28) into the Expression (20) results in the remaining coefficients of the radius R[mm] of the spiral pulley 63 being two (b and c), as shown in the Expression (29) described below.

$$R = f(\theta) = -\left(\frac{r}{L}b + \left(\frac{r}{L}\right)^2 c + \left(\frac{r}{L}\right)^3 (R_{Max} - R_{min})\right)\theta^3 + b\theta^2 + c\theta + R_{Max} \quad (29)$$

Figure 7:
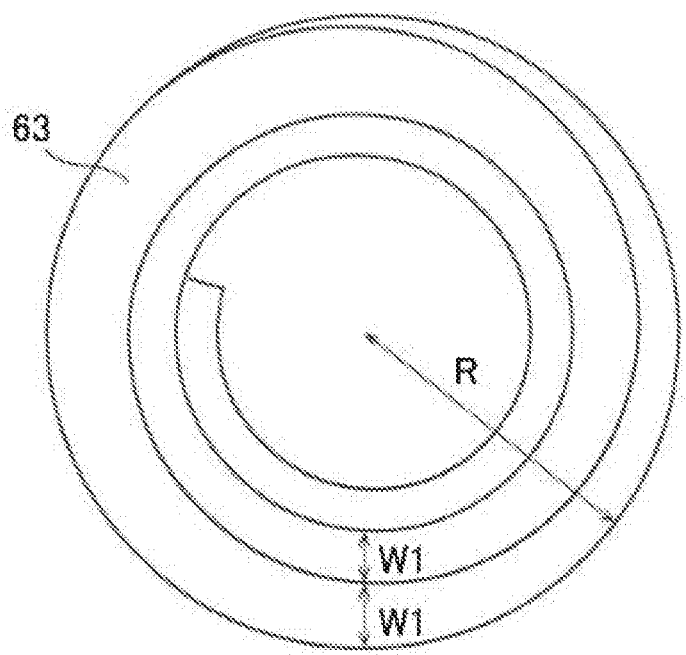
FIG. 7 is a front diagram of a spiral pulley according to the first embodiment.
Figure 8:
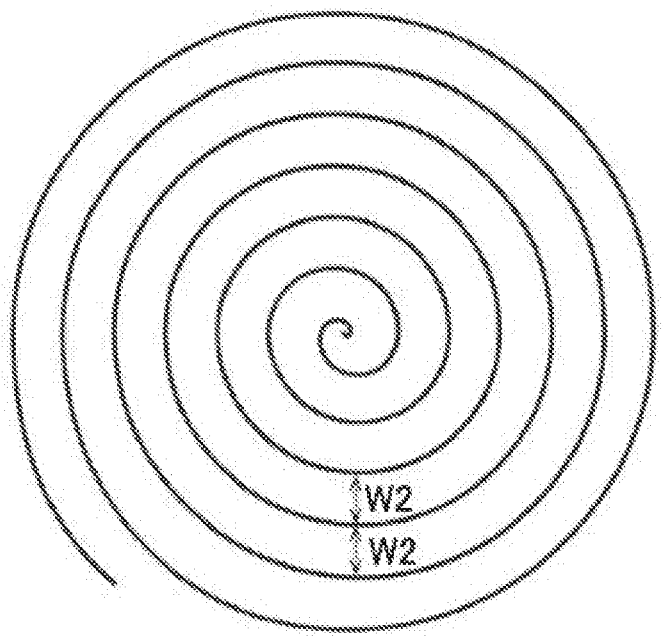
FIG. 8 is a diagram showing an Archimedes' spiral.

The remaining coefficients b and c of the Expression (29) are calculated by: substituting an appropriate value for the coefficients b and c to find the optimal radius R; or automatically calculating using software (e.g., the solver of Excel (registered trademark)) including algorithms to solve mathematical programming problems. As a result, as shown in FIG. 7, the radius R of the spiral pulley 63 is set so that the width W1 between the circumferences changes and differs from the radius of the Archimedes' spiral shown in FIG. 8 (the width W2 between the circumferences is constant).

(Effects of Spiral Pulley's Radius Settings)

Next, with reference to FIG. 9 and FIG. 10, the effects of setting the radius R of the spiral pulley 63 to a radius that differs from the radius of the Archimedes' spiral will be described.

Figure 9:
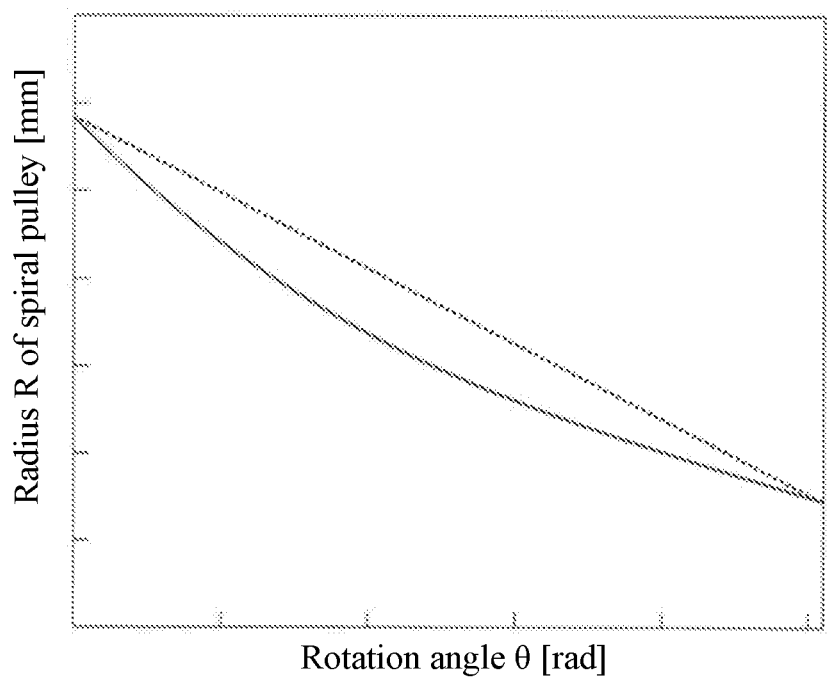
FIG. 9 is a diagram showing a relationship between a rotation angle and a radius of a spiral pulley.

As shown in FIG. 9, when the radius R of the spiral pulley 63 is the Archimedes' spiral (see, the dotted line in FIG. 9), the radius R of the spiral pulley 63 decreases substantially linearly as the rotation angle θ increases. On the other hand, when the radius R of the spiral pulley 63 is set based on the Expression (29) described above (see, the solid line in FIG. 9), the radius R of the spiral pulley 63 decreases so that the degree of the decrease of the radius R becomes gradually smaller as the rotation angle θ increases.

Figure 10:
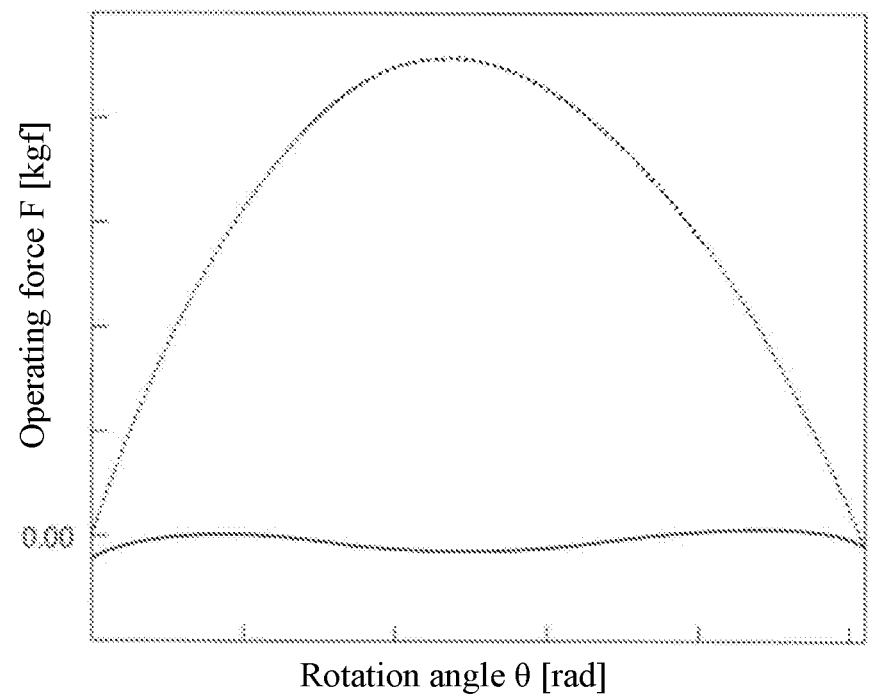
FIG. 10 is a diagram showing a relationship between a rotation angle and an operating force.

Then, as shown in FIG. 10, when the radius R of the spiral pulley 63 is the Archimedes' spiral (dotted line in FIG. 10), it was confirmed that the operating force F [kgf] by the user rapidly increased as the rotation angle θ increased, then reached the maximum (peak), and then decreased. On the other hand, when the radius R of the spiral pulley 63 was set based on the Expression (29) described above (see, the solid line in FIG. 10), it was confirmed that the operating force F[kgf] by the user was approximately 0 [kgf], although it increased or decreased as the rotation angle θ increased or decreased.

(Effects of First Embodiment)

In this first embodiment, the following effects can be obtained.

In the first embodiment, as described above, since the weight W on the X-ray generation unit 50 side is applied to the wire rope 67a wound around the circular pulley 62 having the constant radius r, the wire rope 67a moves along the rotation axis direction of the circular pulley 62 while not moving in a direction crossing the rotation axis direction of the circular pulley 62 as the X-ray generation unit 50 is moved upward and downward. As a result, there is no need to enlarge the exposed portion of the circular pulley 62, so that it is possible to suppress the increase in the size of the diagnostic X-ray apparatus 1. In addition, by setting the radius R of the spiral pulley 63 to a radius (a radius that changes in a spiral manner) that differs from the radius of Archimedes' spiral so that the tensile force of the spring member 61 applied to the wire rope 67b and the weight W on the X-ray generation unit 50 side applied to the wire rope 67a become balanced (or become an approximately balanced state), the tensile force of the spring member 61 applied to the wire rope 67b and the weight W on the X-ray generation unit 50 side applied to the wire rope 67a become balanced (or close to the balance), the user can move the X-ray generation unit 50 upward and downward in the vertical direction with a relatively small force. As a result, it is possible to reduce a burden when the user vertically moves the X-ray generation unit 50. As a result, it is possible to reduce the burden when the user moves the X-ray generation unit 50 upward and downward in the vertical direction while suppressing the increase in the size of the diagnostic X-ray apparatus.

In the first embodiment, as described above, the radius R of the spiral pulley 63 is set to a radius that differs from the radius of the Archimedes' spiral based on the Expression (19) described above. With this, by setting the radius R (spirally varying radius) of the spiral pulley 63 to satisfy the Expression (19) (by setting the radius to differ from the radius of the Archimedes' spiral), the tensile force of the spring member 61 applied to the wire rope 67b and the weight W on the X-ray generation unit 50 side applied to the wire rope 67a can be easily balanced.

In the first embodiment, as described above, in cases where the radius R of the spiral pulley 63 is approximated by the polynomial function of the third-order and the force of the deviation from the state in which the tensile force of the spring member 61 applied to the wire rope 67b and the weight W on the X-ray generation unit 50 side applied to the wire rope 67a become balanced is F, the coefficients included in the approximate expression is determined so that the force F of the deviation becomes substantially zero in the Expression (21). With this, even in cases where the radius R of the spiral pulley 63 cannot be strictly set based on the Expression (19), the radius R (spirally changing radius) of the spiral pulley 63 can be set by using the approximate expression such that the tensile force of the spring member 61 applied to the wire rope 67b and the weight W on the X-ray generation unit 50 side applied to the wire rope 67a are substantially balanced.

In the first embodiment, as described above, in a state in which the radius R of the spiral pulley 63 is approximated by the polynomial function of the third-order and the number of unknown coefficients a, b, c, and d included in the Expression (20) is reduced based on the boundary condition of the rotation angle of the spiral pulley 63, the coefficients included in the approximate expression are determined so that the force F of deviation becomes substantially zero in the Expression (21). With this, it is possible to set radius R of the spiral pulley 63 in which the tensile force of the spring member 61 applied to the wire rope 67b and the weight W on the X-ray generation unit 50 side applied to the wire rope 67a are balanced more accurately, as compared with the case in which the radius R of the spiral pulley 63 is approximated by the polynomial function of the second-order. In addition, since the number of unknown coefficients a, b, c, and d is reduced based on the bounding condition of the rotation angle θ of the spiral pulley 63, it is possible to easily calculate the unknown coefficients.

In the first embodiment, as described above, a wheel 11 that allows the main body 10 to move is provided. With this, in the diagnostic X-ray apparatus 1, it is possible to reduce the burden in cases where when the user moves the X-ray generation unit 50 upward and downward in the vertical direction.

Second Embodiment

Figure 11:
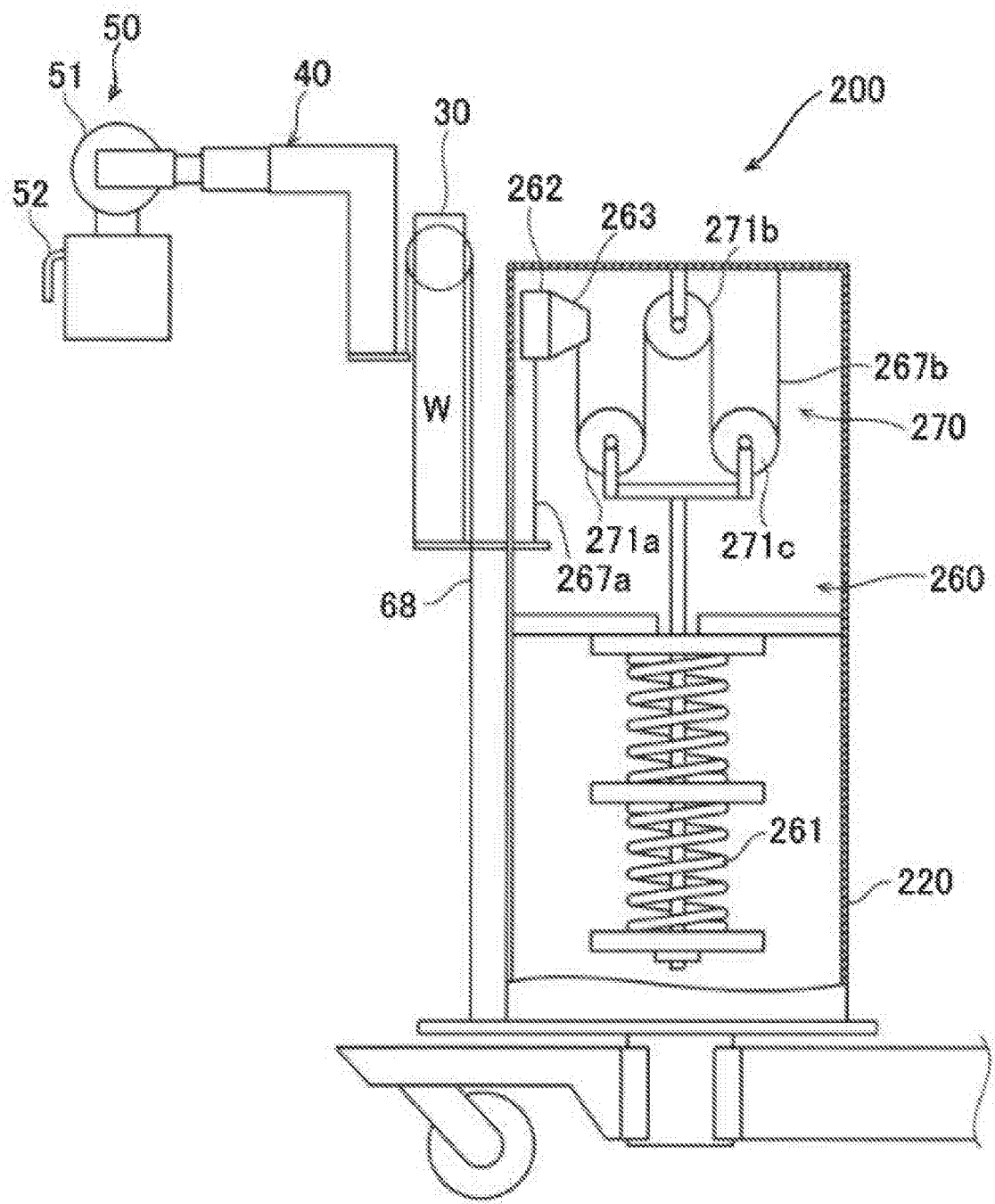
FIG. 11 is a diagram showing a configuration of a diagnostic X-ray apparatus according to a second embodiment.

Next, with reference to FIG. 11, a diagnostic X-ray apparatus 200 according to a second embodiment will be described. In the second embodiment, a balance mechanism 260 is provided with a booster mechanism 270.

In the diagnostic X-ray apparatus 200, the booster mechanism 270 including booster pulley 271a to 271c is provided between the spring member 261 and the spiral pulley 263. Specifically, booster pulleys 271a to 271c are arranged on the wire rope 267b wound around the spiral pulley 263. One end of the wire rope 267b is wound around the spiral pulley 263, and the other end thereof is connected to the supporting unit 220. The booster pulley 271b is fixed to the supporting unit 220. The booster pulleys 271a and 271c are connected to the spring member 261. By providing the booster mechanism 270 in this manner, the winding quantity of the wire rope 267b of the spiral pulley 263 is increased or decreased as the amount of compression of the spring member 261 is increased or decreased. One end of the wire rope 267a is wound around the circular pulley 262, and the other end thereof is connected to the intermediate supporting unit 30. The wire rope 267a and the wire rope 267b are an example of the "first wire rope" and that of the "second wire rope" recited in claims, respectively.

Here, in the second embodiment, when the radius of the spiral pulley 263 is R, the radius of the circular pulley 262 is r, the weight on the X-ray generation unit 50 (the intermediate supporting unit 30) side is W, the spring constant of the spring member 261 is k, the amount of change in the length of the spring member 261 is x, the initial amount of change in the length of the spring member 261 is $x_0$, the rotation angle of the spiral pulley 263 is 0, and the constant due to the boosting force is C, the radius of the spiral pulley 263 is set to a radius that differs from the radius of the Archimedes' spiral based on the following Expression (30).

$$Wr = CkR\left(\int_0^\theta \sqrt{R^2 + \left(\frac{dR}{d\theta}\right)^2}\, d\theta + x_0\right) \quad (30)$$

That is, the Expression (30) is an expression in which the right side of the Expression (19) of the first embodiment with no booster mechanism 270 is multiplied by the constant C. The rest of the configuration of the second embodiment is the same as that of the first embodiment.

(Effects of Second Embodiment)

In the second embodiment, the following effects can be obtained.

In the second embodiment, as described above, the radius is set to a radius that differs from the radius of the Archimedes' spiral based on the Expression (30). As a result, the diagnostic X-ray apparatus 200 provided with the booster mechanism 270 can also set the radius R (radius hat changed) of the spiral pulley 263 in which the tensile force of the spring member 261 applied to the wire rope 267b and the weight W on the X-ray generation unit 50 side applied to the wire rope 267a are balanced, in the same manner as in the diagnostic X-ray apparatus 1 with no booster mechanism 270 according to the first embodiment, by using the Expression (30).

The other effects of the second embodiment are the same as those of the first embodiment.

Third Embodiment

Figure 12:
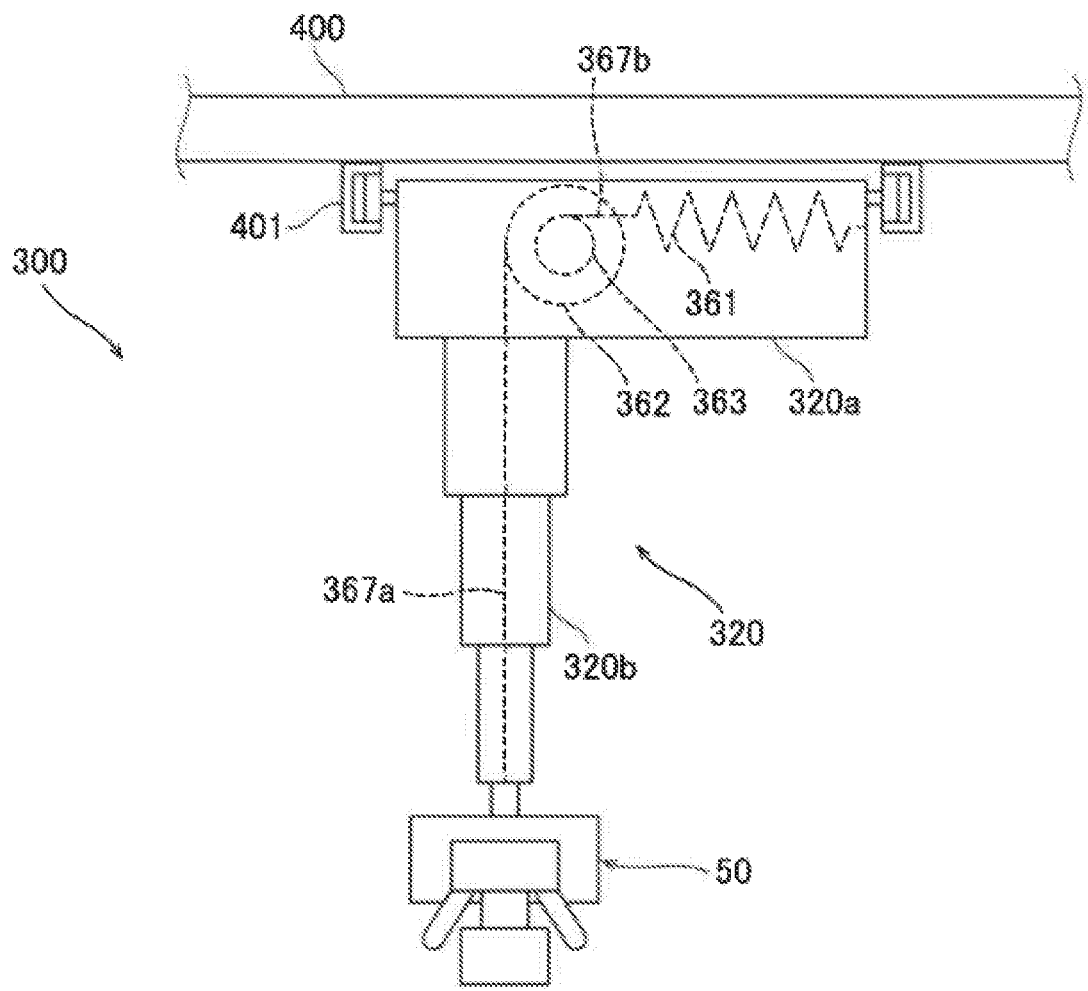
FIG. 12 is a diagram (side view) showing a configuration of a diagnostic X-ray apparatus according to a third embodiment.
Figure 13:
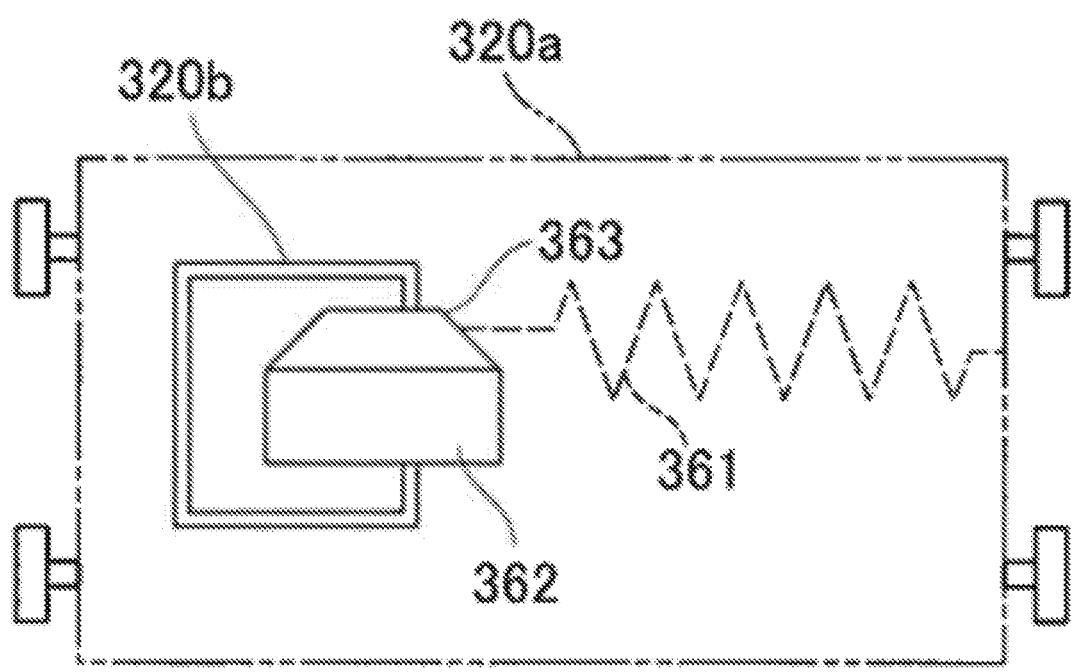
FIG. 13 is a diagram (top view) showing the configuration of the diagnostic X-ray apparatus according to the third embodiment.

Next, with reference to FIG. 12 and FIG. 13, the diagnostic X-ray apparatus 300 according to a third embodiment will be described. In the third embodiment, the supporting unit 320 is suspended from a ceiling 400.

The diagnostic X-ray apparatus 300 is movably arranged on the ceiling rails 401 of the ceiling 400 of the healthcare facility. The supporting unit 320 of the diagnostic X-ray apparatus 300 includes a supporting unit root portion 320a and a telescopic supporting unit 320b. A spring member 361, a circular pulley 362, and a spiral pulley 363 are arranged in the supporting unit root portion 320a. The spring member 361 is arranged along the lower surface of the ceiling 400. One end of the wire rope 367a is wound around the circular pulley 362, and the other end thereof is attached to the X-ray generation unit 50. A wire rope 367a is attached to the X-ray generation unit 50 in a state in which the wire rope 367a penetrates the interior of the telescopic supporting unit 320b. One end of the wire rope 367b is wound around the spiral pulley 363, and the other end thereof is connected to the spring member 361. Note that the wire rope 367a and the wire rope 367b are an example of the "first wire rope" and that of the "second wire rope" recited in claims, respectively. The rest of the configuration of the third embodiment is the same as that of the first embodiment (or the second embodiment).

(Effects of Third Embodiment)

In the third embodiment, the following effects can be obtained.

In the third embodiment, as described above, the supporting unit 320 to which the X-ray generation unit 50 is attached and in which the spring member 361, the circular pulley 362, and the spiral pulley 363 are accommodated is arranged in a state of being suspended from the ceiling 400. As a result, in the diagnostic X-ray apparatus 300 equipped with the supporting unit 320 suspended from the ceiling 400, it is possible to reduce a burden when the user moves the X-ray generation unit 50 upward and downward in the vertical direction. In the diagnostic X-ray apparatus 300 suspended from the ceiling 400, the wire rope 367a penetrates the interior of the supporting unit 320 suspended from the ceiling 400 and is connected to the X-ray generation unit 50. Therefore, as in the third embodiment, by configuring such that the weight W on X-ray generation unit 50 side is be applied to the wire rope 367a wound around the circular pulley 362 having a constant radius r, since the wire rope 367a does not move in a direction crossing the rotational axis direction of the wire rope 367a wound (unwound) around the circular pulley 362, it is possible to prevent the wire rope from coming into contact with the inner surface of the supporting unit 320.

The other effects of the third embodiment are the same as those of the first embodiment.

Modified Embodiment

It should be understood that the embodiments disclosed here are examples in all respects and are not restrictive. The scope of the present invention is shown by claims rather than the descriptions of the embodiments described above, and includes all changes (modifications) within the meaning of claims and equivalents thereof.

For example, in the first to third embodiments described above, an example is shown in which the radius of the spiral pulley is set based on the Expression (19) (or the Expression (30)) described above, but the present invention is not limited thereto. In the present invention, the radius of the spiral pulley may be set based on the Expression and methods other than the Expression (19) and the Expression (30) described above.

In the first to third embodiments described above, the radius of the spiral pulley is approximated by the polynomial function of the third-order, but the present invention is not limited to this. For example, the radius of the spiral pulley may be approximated by a polynomial of the second-order shown in the Expression (31) described below or a polynomial of the fourth-order or higher-order. It may be approximated by a logarithmic function shown in the Expression (32) described below or an exponential function shown in the Expression (33) described below.

$$R = f(B) = a\theta^2 + b\theta + c \quad (31)$$

$$R = f(B) = c \times \log(a\theta^2 + b\theta) \quad (32)$$

$$R = f(B) = c \times e^{a\theta^2 + b\theta} \quad (33)$$

In the first to third embodiments described above, an example is shown in which the spring member composed of a compression-coil spring, but the present invention is not limited to this. For example, the spring member may be composed of a coiled tension spring. Further, the spring member may be composed of two or more spring members.

In the first and second embodiment, an example is shown in which the weight applied to the wire rope wound around the circular pulley is the weight of the intermediate column, but the present invention is not limited to this. For example, in a movable diagnostic X-ray apparatus as described in, e.g., the first and second embodiments, a wire rope wound around a circular pulley described in as, e.g., the third embodiment, may be connected directly to the X-ray generation unit. In this case, the weight applied to the wire rope wound around the circular pulley is the weight of the X-ray generation unit.

In the first to third embodiments, an example is shown in which the first wire rope and the second wire rope are each composed of one piece of a wire rope, but the present invention is not limited to this. For example, the first wire rope and the second wire rope may be each composed of a pair of wire ropes. That is, each of the first wire rope and the second wire rope may be composed of a plurality of wire ropes.

DESCRIPTION OF SYMBOLS 1, 200, 300: Diagnostic X-ray apparatus
10: Main body (diagnostic X-ray apparatus main body)

11: Wheel
20, 220, 320: Supporting unit
50: X-ray generation unit
51: X-ray tube (X-ray source)
61, 261, 361: Spring member
62, 262, 362: Circular pulley
63, 263, 363: Spiral pulley
67a, 267a, 367a: Wire rope (first wire rope)
67b, 267b, 367b: Wire rope (second wire rope)
271a, 271b, 271c: Booster pulley
270: Booster mechanism
400: Ceiling

The invention claimed is:

1. A diagnostic X-ray apparatus comprising:
an X-ray generation unit including an X-ray source for irradiating a subject with X-rays, the X-ray generation unit being movable upward and downward in a vertical direction;
a spring member that expands and contracts as the X-ray generation unit is moved upward and downward;
a circular pulley in which a weight on the X-ray generation unit side is applied to a first wire rope wound around the circular pulley, a radius of the circular pulley being constant; and
a spiral pulley coaxially connected to the circular pulley in a manner as to be rotatable integrally with the circular pulley, a tensile force of the spring member being applied to a second wire rope wound around the spiral pulley, and a radius of the spiral pulley changing in a spiral manner,
wherein the radius of the spiral pulley is set to a radius that differs from a radius of an Archimedes' spiral so that the tensile force of the spring member applied to the second wire rope and the weight on the X-ray generation unit side applied to the first wire rope are balanced.

2. The diagnostic X-ray apparatus as recited in claim 1, wherein when the radius of the spiral pulley is R, the radius of the circular pulley is r, the weight on the X-ray generation unit side is W, a spring constant of the spring member is k, an amount of change in a length of the spring member is x, an initial amount of change in the length of the spring member is $x_0$, and a rotation angle of the spiral pulley is θ, the radius of the spiral pulley is set to a radius that differs from the radius of the Archimedes' spiral based on an Expression (1) described below $$Wr = kR\left(\int_0^\theta \sqrt{R^2 + \left(\frac{dR}{d\theta}\right)^2}\, d\theta + x_0\right). \tag{1}$$

3. The diagnostic X-ray apparatus as recited in claim 2, wherein when the radius R of the spiral pulley is approximated by any one of approximate expressions of a polynomial function, a logarithmic function, and an exponential function of a second-degree or more, a force of deviation from a state in which the tensile force of the spring member applied to the second wire rope and the weight on the X-ray generation unit side applied to the first wire rope are balanced is defined as F, a coefficients included in the approximate expression is defined so that the force F of deviation is substantially zero in an Expression (2) described below $$(W+F)r = kR\left(\int_0^\theta \sqrt{R^2 + \left(\frac{dR}{d\theta}\right)^2}\, d\theta + x_0\right). \tag{2}$$

4. The diagnostic X-ray apparatus as recited in claim 3, wherein when the radius R of the spiral pulley is approximated by a polynomial function of a third-degree shown in an Expression (3) described below and a number of unknown coefficients a, b, c, and d included in the Expression (3) described below is reduced based on a boundary condition of a rotation angle of the spiral pulley, the coefficients included in the approximate expression is determined so that the force F of deviation becomes substantially zero in the Expression (2) described below $$R = f(\theta) = a\theta^3 + b\theta^2 + c\theta + d. \tag{3}$$

5. The diagnostic X-ray apparatus as recited in claim 1, further comprising:
a booster mechanism arranged between the spring member and the spiral pulley, the booster mechanism including a booster pulley,
wherein when the radius of the spiral pulley is R, the radius of the circular pulley is r, the weight on the X-ray generation unit side is W, a spring constant of the spring member is k, an amount of change in a length of the spring member is x, an initial amount of change in the length of the spring member is $x_0$, a rotation angle of the spiral pulley is θ, and a constant number by a booster is C, the radius of the spiral pulley is set to a radius that differs from the radius of the Archimedes' spiral based on an Expression (4) described below $$Wr = CkR\left(\int_0^\theta \sqrt{R^2 + \left(\frac{dR}{d\theta}\right)^2}\, d\theta + x_0\right). \tag{4}$$

6. The diagnostic X-ray apparatus as recited in claim 1, further comprising:
a supporting unit in which the spring member, the circular pulley, and the spiral pulley are accommodated;
a diagnostic X-ray apparatus main body to which the supporting unit is attached; and
a wheel capable of making the diagnostic X-ray apparatus main body movable.

7. The diagnostic X-ray apparatus as recited in claim 1, further comprising:
a supporting unit in which the spring member, the circular pulley, and the spiral pulley are accommodated,
wherein the supporting unit is arranged in a state of being suspended from a ceiling.

* * * * *